United States Patent [19]

Bosies et al.

[11] 4,017,539
[45] Apr. 12, 1977

[54] BIGUANIDE COMPOUNDS AND ANTI-DIABETIC COMPOSITIONS

[75] Inventors: Elmar Bosies, Heppenheim; Kurt Stach, Mannheim-Waldhof; Felix Helmut Schmidt, Mannheim-Seckenheim; Ruth Heerdt, Mannheim-Feudenheim; Helmut Weber, Frankfurt am Main-Schwanheim, all of Germany

[73] Assignee: Boehringer Mannheim G.m.b.H., Mannheim-Waldhof, Germany

[22] Filed: May 7, 1975

[21] Appl. No.: 575,098

[30] Foreign Application Priority Data

June 1, 1974 Germany .......................... 2426683

[52] U.S. Cl. ...................... 260/564 B; 260/501.14; 424/316; 424/326
[51] Int. Cl.² ........................................ C07C 123/00
[58] Field of Search ................. 260/564 B, 501.14; 424/326, 316

[56] References Cited

UNITED STATES PATENTS

| | | | |
|---|---|---|---|
| 3,170,925 | 2/1965 | Doub | 260/564 B |
| 3,270,036 | 8/1966 | Bernstein et al. | 260/564 B |
| 3,471,491 | 10/1969 | Narayanan | 260/564 B |

*Primary Examiner*—Gerald A. Schwartz
*Attorney, Agent, or Firm*—Burgess, Dinklage & Sprung

[57] ABSTRACT

New biguanide compounds of the formula:

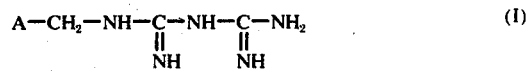

wherein A is saturated or unsaturated cycloaliphatic hydrocarbyl, and the physiologically compatible salts thereof; display outstanding anti-diabetic effectiveness in the treatment of diabetes mellitus, without showing the typical side effects of biguanide treatment, viz., lactacidosis.

1 Claim, No Drawings

BIGUANIDE COMPOUNDS AND ANTI-DIABETIC COMPOSITIONS

The present invention relates to new biguanide compounds and to therapeutic compositions containing them.

Of the 1-substituted biguanides, three compounds are at present used for the treatment of diabetes mellitus, namely, 1,1-dimethylbiguanide (metformin), 1-butylbiguanide (buformin) and 1-phenethylbiguanide (phenformin).

It is known that biguanides, especially 1-phenethylbiguanide, in the course of a predispositioning disease, such as kidney insufficiency or cardiac insufficiency, can give rise to a lactacidosis, and there has thus been a need for compounds not including this side effect.

The present invention provides anti-diabetically-active biguanides which have such improved compatibility.

The biguanides of the invention have the formula:

$$A-CH_2-NH-\underset{\underset{NH}{\|}}{C}-NH-\underset{\underset{NH}{\|}}{C}-NH_2 \qquad (I)$$

wherein A is saturated or unsaturated cycloaliphatic hydrocarbyl, and the physiologically compatible salts thereof.

The substituent A is preferably a saturated cycloaliphatic radical containing 3 to 7 carbon atoms or an unsaturated cycloaliphatic hydrocarbon radical containing one or two double bonds and 5 to 7 carbon atoms; the preferred unsaturated cycloaliphatic hydrocarbon radical containing two double bonds is the cyclohexa-1,4-dien-1-yl radical.

The new compounds of general formula (I) according to the present invention can be prepared, for example, by one of the following methods:

a. reaction of an amine of the general formula:

$$A\text{-}CH_2\text{-}NH_2 \qquad (II),$$

wherein A has the same meaning as above, or of a salt thereof, with a biguanide derivative of the general formula:

$$H_2N-\underset{\underset{NH}{\|}}{C}-NH-\underset{\underset{NY}{\|}}{C}-X \qquad (III),$$

wherein X is an amino, mercapto or pyrazole-1-yl radical or an —OR or —SR radical and Y is a hydrogen atom or X and Y can together represent a further valency bond and R is a benzyl or lower alkyl radical, or with a salt thereof; or b. reaction of a compound of the general formula:

$$A-CH_2-NH-\underset{\underset{NY}{\|}}{C}-X_1 \qquad (IV),$$

wherein $X_1$ is an amino or mercapto group or an —OR or —SR radical and A, Y and R have the same meanings as above or Y and $X_1$ can together also represent a further valency bond, or of a salt thereof, with a urea derivative of the general formula:

$$H_2N-\underset{\underset{NY}{\|}}{C}-X_1 \qquad (V),$$

wherein $X_1$ and Y have the same meanings as above, with the proviso that one of the $X_1$ substituents must be an amino group, or with a salt thereof; or c. reaction of a compound of the general formula:

$$A-CH_2-N=\underset{\underset{X_1}{|}}{C}-NH-\underset{\underset{X_1}{|}}{C}=N-Y \qquad (VI),$$

wherein A, Y and $X_1$ have the same meanings as above but with the proviso that both substituents $X_1$ cannot simultaneously be amino groups, with ammonia or with an ammonium salt; whereafter, if desired, the compound obtained is converted into a physiologically compatible acid-addition salt.

The lower alkyl radical of the substituent R can contain up to 4 carbon atoms.

The processes according to the present invention are preferably carried out by warming the reaction compounds in an inert solvent.

Process a) is, when reacting an amino salt with dicyandiamide, carried out in an inert solvent, for example, benzene, toluene, xylene or o-dichlorobenzene, at the boiling temperature of the solvent used or in aqueous hydrochloric acid or under reflux in an alcohol, for example methanol, ethanol, isopropanol or n-butanol. The reaction components can also be reacted by mixing them together and then heating the mixture in the melt at a temperature between 120° and 200° C. When reacting an amine with a salt of N-amidinopyrazol-1-yl-carboxamidine, as solvent there is preferably used, chloroform, chloroform/ethanol, ethanol or ethanol/water. The temperature used is preferably within the range of from 20° to 80° C. As solvent for the reaction of an amine with a salt of an amidinourea derivative, there is preferably used toluene or xylene at a reaction temperature of from 100° to 160° C. However, the reaction can also be carried out in water. When using an S-methyl compound, the end of the reaction can be recognized by a decrease of the evolution of methyl mercaptan. The reaction of the amine with biguanide can be carried out under reflux in 10 to 15% hydrochloric acid.

Process b) is carried out at an elevated temperature with the use of an alcohol or solvent, for example of methanol, ethanol, isopropanol, n-butanol or ethylene glycol, possibly with the addition of water. The solvent used can possibly also be a high boiling point, non-polar solvent, for example, toluene, xylene, anisole or di-n-butyl ether. Instead of cyanamide or derivative thereof, there can also be used the corresponding sodium salts and the reaction components can also be reacted in the melt.

Process c) is, in the case of the reaction of an amidino-thiourea or dithiobiuret of general formula (VI) with ammonia, carried out with the use of an alcohol as solvent, for example, of methanol, ethanol or isopropanol, possibly in admixture with water, at a reaction temperature of from 20° to 80° C. When reacting O- or S-substituted derivatives of general formula (VI) with ammonia, as solvent it is best to use an alcohol, for example methanol, ethanol or isopropanol, possibly in admixture with water. The reaction is usually carried out in a closed vessel at a temperature of from 100° to 150° C. A cyanoguanidine derivative of general formula (VI) is reacted with an ammonium salt in a high boiling point solvent. However, the reaction components can also be reacted together in the melt at a temperature of from 140° to 160° C. The ammonium salt used can be, for example, ammonium chloride, bromide or iodide or an ammonium sulphonate, for example, ammonium benzene sulphonate. As solvent, there can be used, for example, n-butanol, dimethyl sulphoxide or o-dichlorobenzene.

When the starting materials in the above-described processes are used in the form of salts, the salts used are generally those with inorganic or organic acids, preferably hydrohalic acids, carbonic acid, sulphuric acid, nitric acid or methane-sulphonic acid. These salts can be reacted in the presence of bases, for example, tertiary amines, for example trimethylamine, triethylamine, pyridine or quinoline. However, alkali metal alkoxides, preferably sodium methylate, can also be used.

In those cases in which one of the reaction components contains a sulfur atom, for example, thiourea and dithiobiuret derivatives, the above-described processes can, if desired, be carried out in the presence of heavy metals or of heavy metal oxides. Examples of appropriate heavy metal oxides include mercury and lead oxides and the heavy metal can be, for example, Raney nickel.

The new compounds according to the present invention are usually isolated as their mono- or disalts with mineral acids. The free bases can be liberated from the salts with a strong base and converted into a different salt by reaction with another acid.

The pharmacologically compatible salts are usually obtained from the free bases of general formula (I) by reaction with non-toxic, inorganic or organic acids, for example, with hydrochloric acid, sulphuric acid, phosphoric acid, hydrobromic acid, acetic acid, lactic acid, citric acid, oxalic acid, malic acid, salicylic acid, malonic acid or succinic acid.

The blood sugar-lowering pharmaceutical compositions also provided according to the present invention can be any of the conventional forms suitable for oral administration, for example, tablets, dragees, capsules, suspensions and the like and are preferably compositions with a delayed release of the active material. For this purpose, the active material is mixed with a solid or liquid carrier material and subsequently brought into the desired from. Examples of solid carrier materials include lactose, starch, talc, calcium hydrogen phosphate, aluminium hydroxide, cellulose derivatives, gelatine, waxes, resins, magnesium stearate and swelling materials; as liquid carrier materials, there can be used, for example, organic liquids, such as polyethylene glycol or higher alcohols in which the active material is not dissolved.

The following examples are given for the purpose of illustrating the present invention:

Example 1

Preparation of (1-Cyclopentylmethyl)-biguanide hydrochloride 13.5 g. cyclopentylmethylamine hydrochloride and 8.4 g. dicyandiamide are heated under reflux for 6 hours in 60 ml. xylene. After cooling, the xylene is decanted off and the residue is dissolved in hot ethanol. The solution obtained is treated with active charcoal, hot filtered and the filtrate mixed, after cooling, with diethyl ether. The precipitate obtained is filtered off with suction and recrystallized from isopropanol. There are obtained 13.2 g. (about 63% of theory) 1-(cyclopentylmethyl)-biguanide hydrochloride; m.p. 223° – 225° C.

In an analogous manner, the following compounds are obtained by the reaction of dicyandiamide with the mentioned amine salt:

a. from cyclopent-2-en-1-ylmethylamine hydrochloride, there is obtained 1-(cyclopent-2-en-1-ylmethyl)-biguanide hydrochloride; m.p. 214° – 215° C., after recrystallization from ethanol; yield 58% of theory;

b. from cyclohex-3-en-1-ylmethylamine hydrochloride, there is obtained 1-(cyclohex-3-en-1-ylmethyl)-biguanide hydrochloride; m.p. 180° – 182° C., after recrystallization from isopropanol; yield 59% of theory; and c. from cyclohexa-1,4-dien-1-ylmethylamine hydrochloride, there is obtained 1-(cyclohexa-1,4-dien-1-ylmethyl)-biguanide dihydrochloride; m.p. 203° – 207° C., after recrystallization from isopropanol/diethyl ether; yield 38% of theory. The monohydrochloride is dissolved in ethanol and the dihydrochloride thereof precipitated out by the addition of ethereal hydrochloric acid.

Example 2

Preparation of 1-(Cyclohexylmethyl)-biguanide hydrochloride

A mixture of 15 g. cyclohexylmethylamine hydrochloride and 8.4 g. dicyandiamide is slowly heated to 160° C. in an oilbath. The commencement of the reaction can be recognized by the melting of the reaction components and an increase of the temperature. Subsequently, the reaction mixture is maintained for one hour at 160° C. After cooling, the melt cake is recrystallized from isopropanol, with the use of active charcoal. There are obtained 12.85 g. (about 55% of theory) 1-(cyclohexylmethyl)-biguanide hydrochloride; m.p. 170° – 172° C.

Example 3

Preparation of 1-(Cyclohex-1-en-1-ylmethyl)-biguanide hydrochloride

A mixture of 11.1 g. cyclohex-1-en-1-ylmethylamine and 18.8 g. N-amidinopyrazol-1-yl-carboxamidine hydrochloride is boiled under reflux for 4 hours in 150 ml. 50% ethanol. Subsequently, the reaction mixture is evaporated, the residue is taken up in water and this solution is shaken out several times with chloroform and diethyl ether. The aqueous phase is then evaporated and the residue is dried and recrystallized from isopropanol. There are obtained 8.34 g. (about 36% of theory) 1-(cyclohex-1-en-1-ylmethyl)-biguanide hydrochloride; m.p. 205° – 208° C.

In an analogous manner, the following compounds are obtained by the reaction of N-amidinopyrazol-1-ylcarboxamidine hydrochloride with the mentioned amine:

a. with cyclopropylmethylamine, there is obtained 1-(cyclopropylmethyl)-biguanide hydrochloride; m.p.

214°–216° C., after recrystallization from isopropanol; yield 66% of theory:

b. with cyclobutylmethylamine, there is obtained 1-(cyclobutylmethyl)-biguanide hydrochloride; m.p. 212°–213° C., after recrystallization from isopropanol; yield 47% of theory:

c. with cyclohex-2-en-1-ylmethylamine, there is obtained 1-(cyclohex-2-en-1-ylmethyl)-biguanide hydrochloride; m.p. 170°–172° C., after recrystallization from isopropanol; yield 42% of theory;

d. with cycloheptylmethylamine, there is obtained 1-(cycloheptylmethyl)-biguanide hydrochloride; m.p. 171°–173° C., after recrystallization from isopropanol; yield 35% of theory;

e. with cyclopent-1-en-1-ylmethylamime, there is obtained 1-(cyclopent-1-en-1-ylmethyl)-biguanide hydrochloride; m.p. 195°–198° C., after recrystallization from isopropanol; yield 16% of theory;

The cyclopent-1-en-1-ylmethylamine used as starting material is obtained by the reduction of cyclopentanone cyanohydrin with lithium aluminium hydride to 1-aminomethyl-cyclopentan-1-ol (b.p. 85°–93° C./12 mm.Hg.) and the subsequent splitting off of water therefrom with thionyl chloride in toluene to give cyclopent-1-en-1-ylmethylamine; b.p. 50°–55° C./12 mm.Hg.

f. with cyclohept-1-en-1-ylmethylamine, there is obtained 1-(cyclohept-1-en-1-ylmethyl)-biguanide hydrochloride; m.p. 182°–185° C., after recrystallization from isopropanol; yield 37% of theory.

By the reduction of cycloheptanone cyanohydrin with lithium aluminium hydride, there is obtained 1-aminomethyl-cycloheptan-1-ol (b.p. 117°–120° C./12 mm.Hg.) from which, by splitting off water with thionyl chloride in toluene, there is prepared cyclohept-1-en-1-ylmethylamine (b.p. 40°–45° C./0.2 mm.Hg).

g. from cyclohept-2-en-1-ylmethylamine, there is obtained 1-(cyclohept-2-en-1-ylmethyl)-biguanide hydrochloride; m.p. 144°–148° C., after recrystallization from isopropanol; yield 36% of theory.

The cyclohept-2-en-1-ylmethylamine (b.p. 75°–78° C./12 mm.Hg.) used as starting material is obtained by the reduction of cyclohept-2-en-1-carbonitrile (b.p. 80°–85° C./12 mm.Hg.) with lithium aluminium hydride. The cyano compound can be prepared by the reaction of 3-bromocyclohept-1-ene with potassium cyanide.

Example 4

Preparation of
1-(Cyclopent-3-en-1-ylmethyl)-biguanide dihydrochloride 12.2 g. amidino-S-methylisothiourea sulphate are added to a solution of 4.9 g. cyclopent-3-en-1-ylmethylamine in 100 ml. xylene. The reaction mixture is maintained at 140° C. for 3 hours. After cooling, the residue is taken up in aqueous ethanol, filtered and the biguanide precipitated out with an ammoniacal solution of copper sulphate. The precipitate is filtered off with suction and dissolved in dilute hydrochloric acid. After passing hydrogen sulphide, the reaction mixture is filtered with suction and the filtrate completely evaporated. The residue obtained is first recrystallized from isopropanol/diethyl ether and then from isopropanol/ethanol. There is obtained 1-(cyclopent-3-en-1-ylmethyl)-biguanide dihydrochloride in a yield of 20% of theory; m.p. 204°–208° C.

The blood sugar reducing activity of test compounds representative of this invention was measured in guinea pigs following i.p. administration of aqueous solutions of the test compounds. In each instance, the threshold dosage, i.e., the lowest dosage of compound required to produce a significant reduction in the blood sugar level, was determined. A known anti-diabetic, "Metformin," was included for comparison purposes.

The results are set forth in the Table, below.

TABLE

| Test Compound | Prep. Ex. | Threshold Dosage (i.p.) In mg/kg |
|---|---|---|
| 1-(Cyclopropylmethyl)-biguanide-hydrochloride | 3(a) | 25 |
| 1-(Cyclobutylmethyl)-biguanide hydrochloride | 3(b) | 15 |
| 1-(Cyclopentylmethyl)-biguanide-hydrochloride | 1 | 15–20 |
| 1-(Cyclopent-1-en-1-ylmethyl)-biguanide-hydrochloride | 3(c) | 15 |
| 1-(Cyclopent-3-en-1-ylmethyl)-biguanide-dihydrochloride | 4 | 15 |
| 1-(Cyclopent-2-en-1-ylmethyl)-biguanide-hydrochloride | 1(a) | 20–30 |
| 1-(Cyclohexylmethyl)-biguanide-hydrochloride | 2 | 15–20 |
| 1-(Cyclohex-3-en-1-ylmethyl)-biguanide-hydrochloride | 1(b) | 15 |
| 1-(Cyclohex-2-en-1-ylmethyl)-biguanide-hydrochloride | 3(c) | 20 |
| 1-(Cyclohex-1-en-1-ylmethyl)-biguanide-hydrochloride | 3 | 20 |
| 1-(Cyclohexa-1,4-dien-1-ylmethyl)-biguanide-dihydrochloride | 1(c) | 15 |
| 1-(Cycloheptylmethyl)-biguanide-hydrochloride | 3(d) | 20 |
| 1-(Cyclohept-1-en-1-ylmethyl)-biguanide-hydrochloride | 3(f) | 30 |
| 1-(Cyclohept-2-en-1-ylmethyl)-biguanide-hydrochloride | 3(g) | 40 |
| Metformin* | | 100 |

*1.1-dimethyl biguanide hydrochloride

The novel biguanide compounds of the invention can be administered in conventional fashion and appropriate dosages may be in the order of 50 mg applied from 1 to 3 times a day. The maximal blood sugar depressing effect is normally reached about 4 to 6 hours after application and disappears after about 6 to 8 hours. In this respect the compounds of the invention are utilized in a manner analogous to the methods of application of the known biguanide-hydrochloride compound sold under the generic name Phenformin and commercially under the name "Dipar" by Farbwerke Hoechst AG, Frankfurt, Germany. Typically, the active compound is applied in the form of dragees with one dragee taken after breakfast on the first day and gradually increased to up to three dragees per day at mealtimes.

It will be understood that the specification and examples are illustrative but not limitative of the present invention and that other embodiments within the spirit and scope of the invention will suggest themselves to those skilled in the art.

What is claimed is:
1. 1-(cyclobutylmethyl)-biguanide-hydrochloride.

* * * * *